United States Patent [19]
Lucas et al.

[11] Patent Number: 5,291,791
[45] Date of Patent: Mar. 8, 1994

[54] CAPACITANCE FLOW METER

[75] Inventors: Gary P. Lucas, Hilton; Sam Simonian, Welwyn Garden City, both of England

[73] Assignee: Schlumberger Technology Corporation, Houston, Tex.

[21] Appl. No.: 879,824

[22] Filed: May 7, 1992

[30] Foreign Application Priority Data

May 8, 1991 [GB] United Kingdom ............... 9109957

[51] Int. Cl.$^5$ ............................................. G01F 1/56
[52] U.S. Cl. ............................. 73/861.08; 73/861.04
[58] Field of Search ................. 73/861.08, 861.04; 324/686, 687, 688, 690

[56] References Cited

U.S. PATENT DOCUMENTS

| | | | |
|---|---|---|---|
| 4,074,184 | 2/1978 | Dechene et al. | 324/690 |
| 4,354,219 | 10/1982 | Akita | 73/861.08 |
| 4,953,408 | 9/1990 | Appel et al. | 73/861.16 |
| 5,017,879 | 5/1991 | Lucas et al. | 324/686 |
| 5,130,661 | 7/1992 | Beck et al. | 324/687 |

Primary Examiner—Richard E. Chilcot, Jr.
Assistant Examiner—Elizabeth L. Dougherty
Attorney, Agent, or Firm—John J. Ryberg; Wayne I. Kanak

[57] ABSTRACT

A multi-electrode capacitive apparatus for measuring multi-phase flows comprising a pipe through which the flow is directed having the electrodes, typically ten in number, disposed around an outer surface thereof, sensing means being provided for connection to each electrode by means of a switching arrangement, the switching arrangement being operable to vary the connections of the electrodes to the sensing means such that the electric field seen within the pipe rotates; averaging means being provided to determine the average capacitance measured over an integer number of rotations. The pipe can be formed from a material having substantially the same dielectric constant as the flowing material and is of sufficient thickness to optimise the angular sensitivity of the device for flow at the pipe wall. Typically, the internal radius of the pipe is about 0.7 of the radius of the electrode arrangement.

9 Claims, 13 Drawing Sheets r/R = 0.8 r/R = 0.7

CAPACITANCE FLOW METER

The present invention relates to a capacitance flow meter for measuring multi-phase flows and particularly, though not exclusively, to a flow meter for measuring the void fraction in multi-phase flows.

The invention is particularly applicable to a case in which the multi-phase flow comprises a continuous liquid phase and a dispersed gas phase such as might be found in products flowing from oil wells. It has been previously proposed to measure such flow by means of capacitive sensors comprising capacitance electrodes based around a pipe containing the flowing material, the measured capacitance indicating the nature of the flow. However, these previously proposed designs have suffered from problems in that the field generated in the pipe is not uniform, especially in the region of the pipe adjacent the capacitance electrodes. This in turn means that the sensitivity of the device in the region near the electrodes is variable and FIG. 1 shows the variation of sensitivity of such a device for measurements made in a circular pipe having capacitance electrodes arranged round an outer surface thereof, the measurements being made at a radius which is 0.9 of the radius of the electrode arrangement.

The above problem has been recognised previously and attempts have been proposed to remove such a problem. USSR Patent 548,798 proposes that the capacitive electrodes curve away from the pipe, the amount of curvature being related to the pipe thickness in order that the field generated in the pipe might be as uniform as possible. USSR Patent 566,174 proposes bow shaped plates and zero electrodes adjacent thereto for generating the field in the pipe.

European Patent Application 0,308,004 (assigned to Schlumberger Limited et al, incorporated herein by reference) describes an arrangement in which the variation in sensitivity of a capacitive flow meter is reduced by providing the meter in the form of body defining a flow passage which is formed from a material of substantially similar dielectric constant to the material being measured, the thickness of which is such that the electrodes are separated from the flowing material by sufficient distance to ensure that the flow is confined to a region of relatively uniform field, thus reducing the angular sensitivity of the device. The typical thickness of the body is 30% of the radius of the outer surface on which the electrodes are mounted. However, even with this arrangement there is a variation in sensitivity with angular position at the outer regions of the body. FIG. 3 shows the typical variation in sensitivity at the wall of the pipe wherein the radius of the flowing region is 0.7 of the radius of the electrode arrangement.

The present invention has arisen in an attempt to improve the uniformity of sensitivity of a capacitance flow meter beyond that already proposed in the applicant's prior European Patent Application.

According to the present invention, there is provided a multi-electrode capacitive apparatus for measuring multi-phase flows comprising: a) a pipe through which the flow is directed having the electrodes disposed around a wall thereof, b) a switching arrangement, c) sensing means for connection to each electrode by means of said switching arrangement, said switching arrangement being operable to vary the connection of the electrodes to the sensing means such that an electric field seen within said pipe rotates, wherein said electrodes are connected so as to form an excitation group of adjacent electrodes and a detection group of adjacent electrodes, the excitation group and the detection group being of approximately the same size, and d) averaging means for determining an average capacitance measured over an integer number of rotations independently of phase distribution in the pipe.

The present invention has the advantage that any angular sensitivity inherent in the arrangement is removed by effectively rotating the field seen within the pipe relative to the flow therethrough and averaging the capacitance measured so as to remove the angular variation in sensitivity produced by the device.

The provision of a multi-electrode arrangement and the switching arrangement means that the device can be operated to obtain the optimum field within the pipe and rotate it by adjustment at the switching arrangement so as to optimise the averaging period without the requirement for physical rotation of the electrode arrangement This is particularly useful where access to the pipe is restricted.

Preferably, the pipe is formed from a material having substantially the same dielectric constant as the flowing material and is of sufficient thickness to optimise the angular sensitivity of the device for flow at the pipe wall. Typically, the internal radius of the pipe is about 0.7 of the radius of the electrode arrangement.

Conveniently, a ten electrode arrangement is provided, typically the electrodes being equally spaced around the pipe and each electrode typically subtending 36° of arc. For a ten electrode arrangement, it is preferred that for any one position a group of four electrodes are connected to the excitation terminal of measurement circuitry, one electrode connected to earth is provided on either side of this group as a guard and the remaining four electrodes are connected to the virtual earth terminal of the measurement circuitry. Preferably the 4:1:1:4 or 144°:36°:36°:144° relationship is substantially maintained for these functional groups irrespective of the actual number of electrodes present. The axial length of the electrodes is selected to optimise the averaging of measurements in the relevant conditions.

In such an arrangement, the effective rotation of the field can be achieved by transferring the setting of each electrode to its adjacent neighbour in a given direction, this process being repeated until the original position settings are resumed.

The averaging means can typically average measurements taken over one or more, rotations of the field according to requirements.

The present invention will now be described by way of example with reference to the accompanying drawings, in which.

Figure 10:
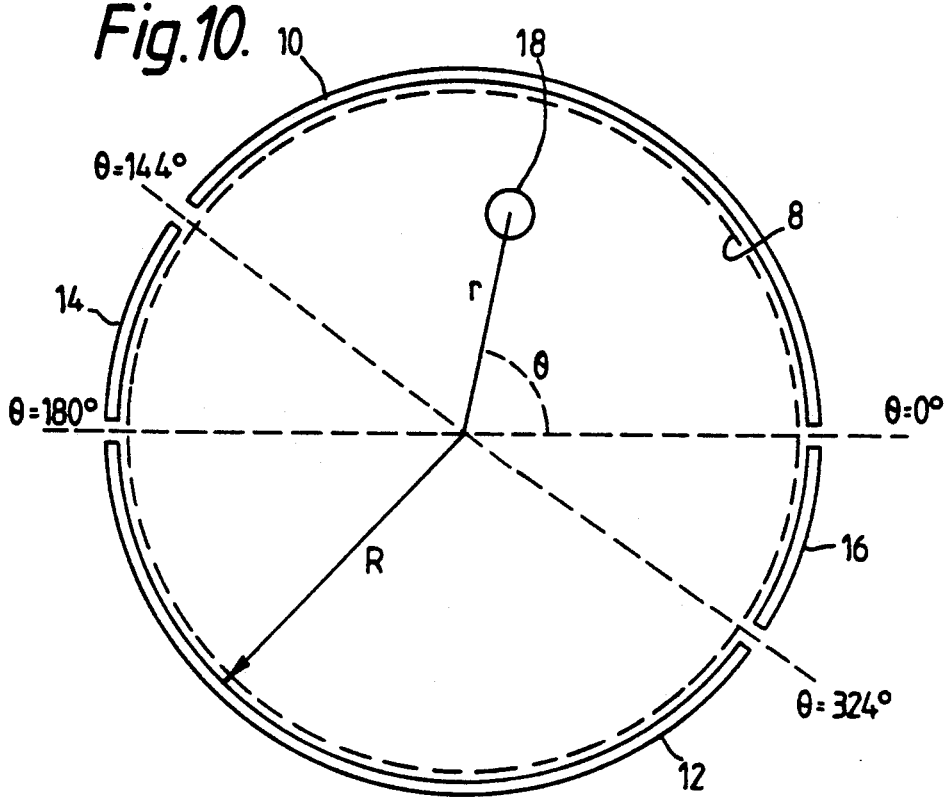
FIG. 10 shows the experimental set up used to obtain the results in FIGS. 1-9.

Referring now to the drawings, FIGS. 1-9 show variation in sensitivity of the device shown in FIG. 10 at different radii within the pipe. The device shown in FIG. 10 comprises an oil filled pipe 8 having a circular capacitive electrode arrangement of radius R provided around the outside thereof. The electrodes comprise an excitation electrode 10 subtending an angle of 144°, a virtual earth current detection electrode 12 also subtending an angle of 144° diametrically opposed to the excitation electrode 10, and a pair of earth guard electrodes 14, 16 separating the electrodes 12, 14 and each subtending an angle of 36°. The capacitance measured by this device is recorded when a dielectric cylinder 18 representing a bubble is rotated about the centre of the pipe 8 at predetermined radii r, the results being plotted in FIGS. 1-9.

Figure 1:
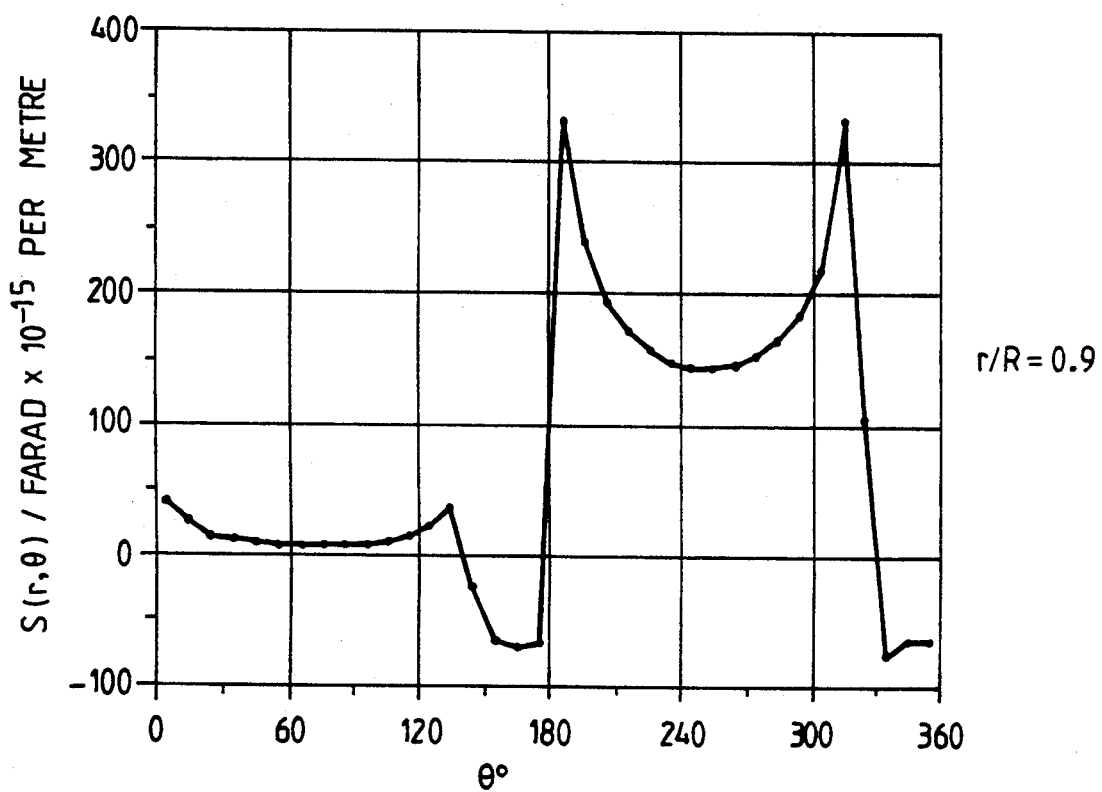
FIGS. 1-9 show the variation in sensitivity $(s(r,\theta)/(\text{Farad} \times 10^{-15}$ per meter) related to angular position $(\theta°)$ for measurements made at various radii within a circular arrangement of capacitive electrodes and radius (R)
Figure 2:
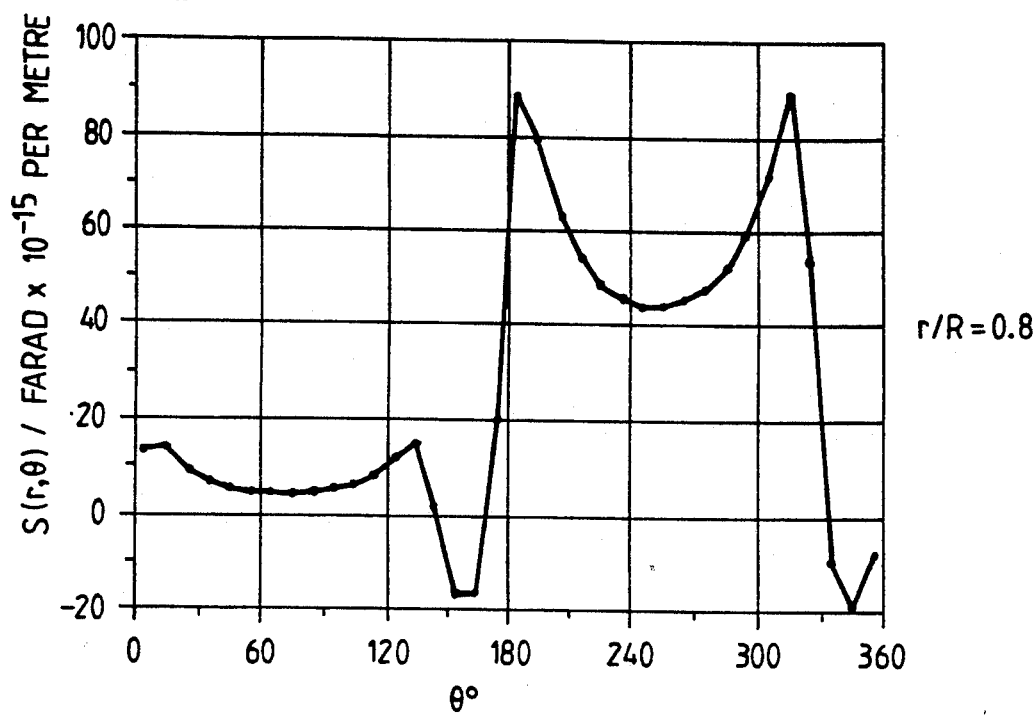
Figure 3:
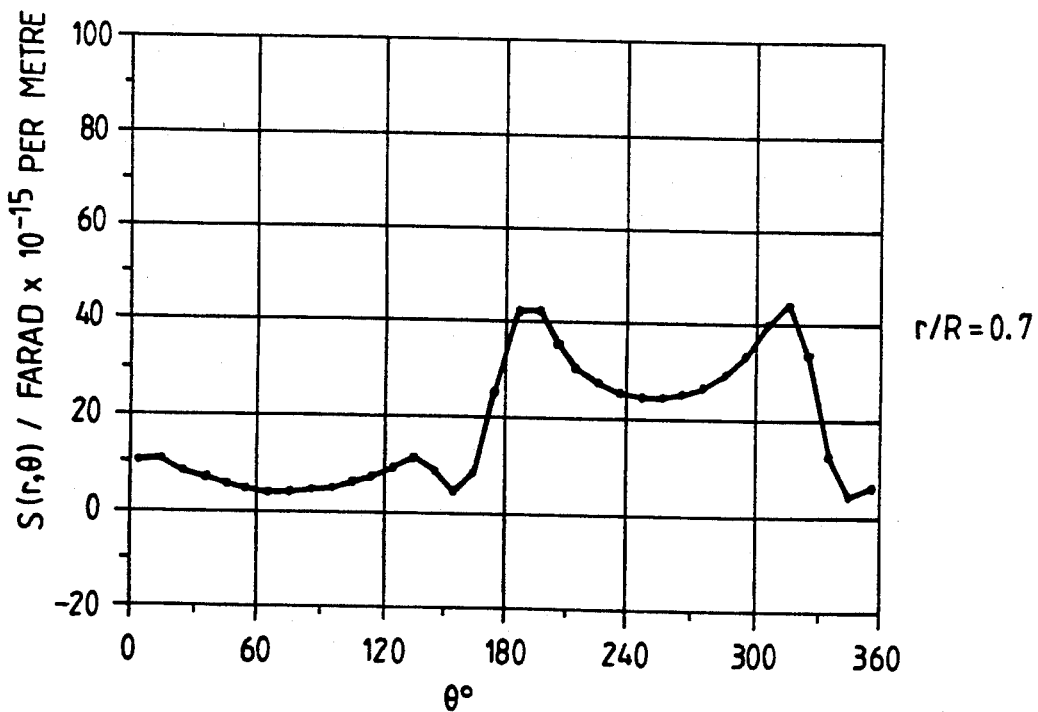
Figure 4:
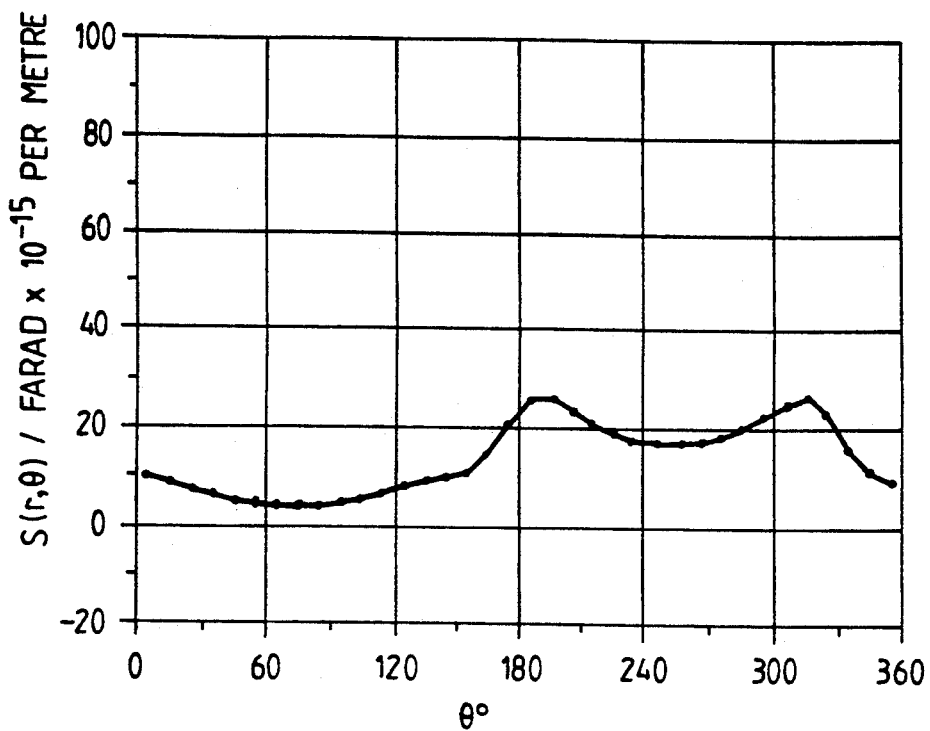
Figure 5:
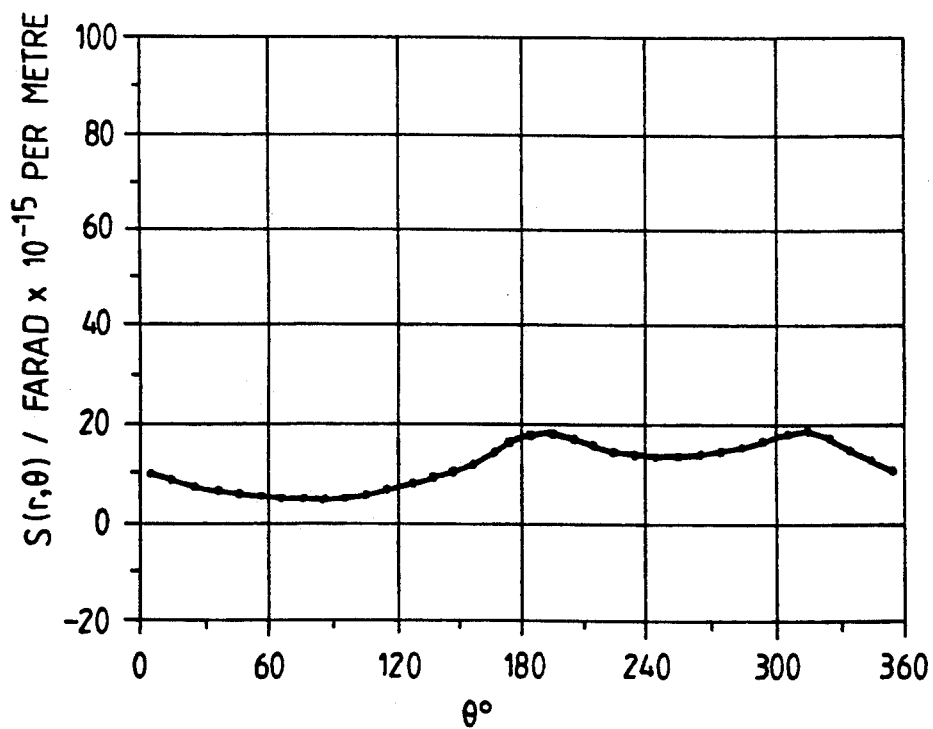
Figure 6:
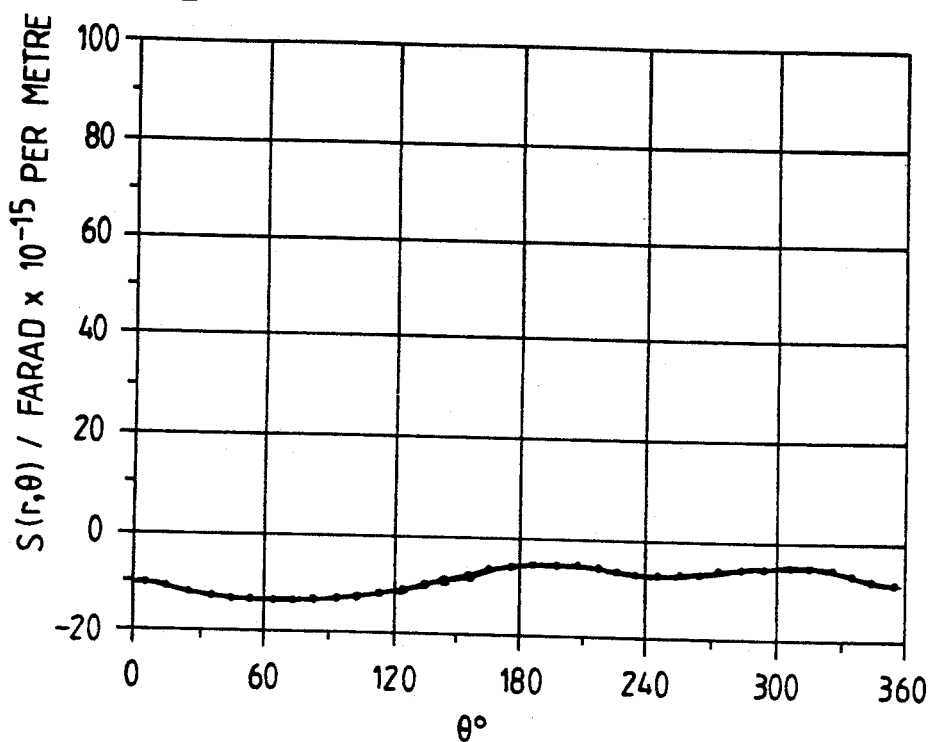
Figure 7:
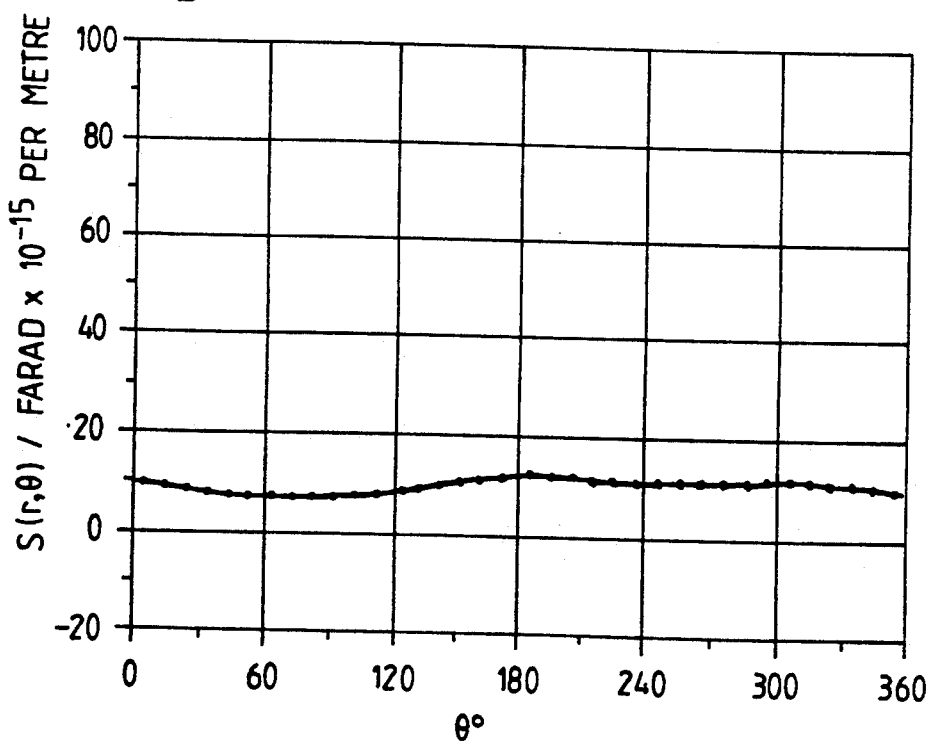
Figure 8:
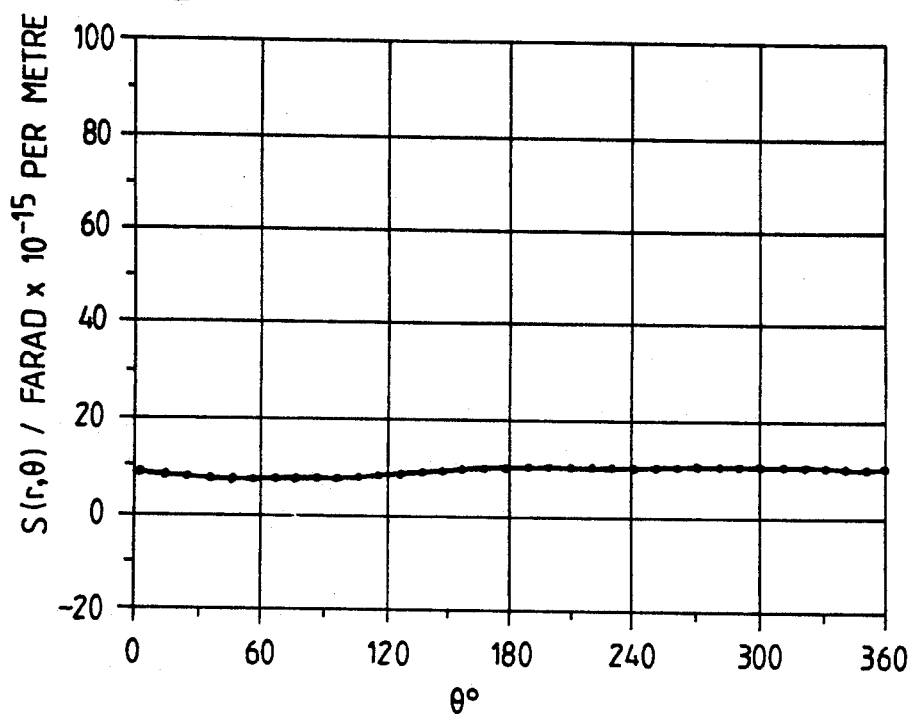
Figure 9:
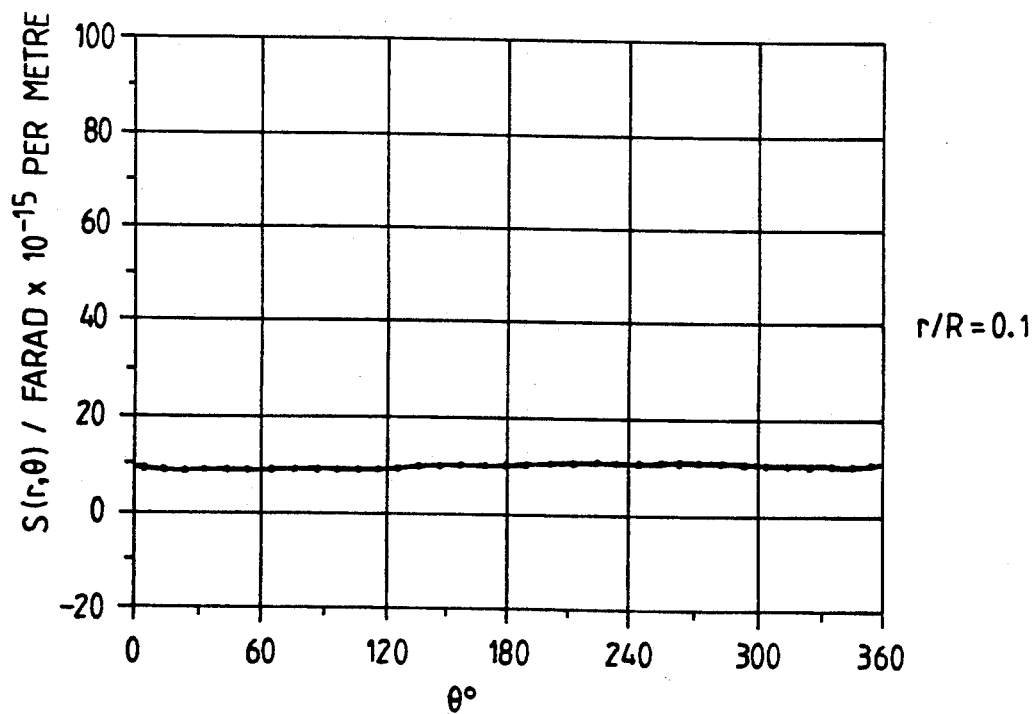
Figure 11:
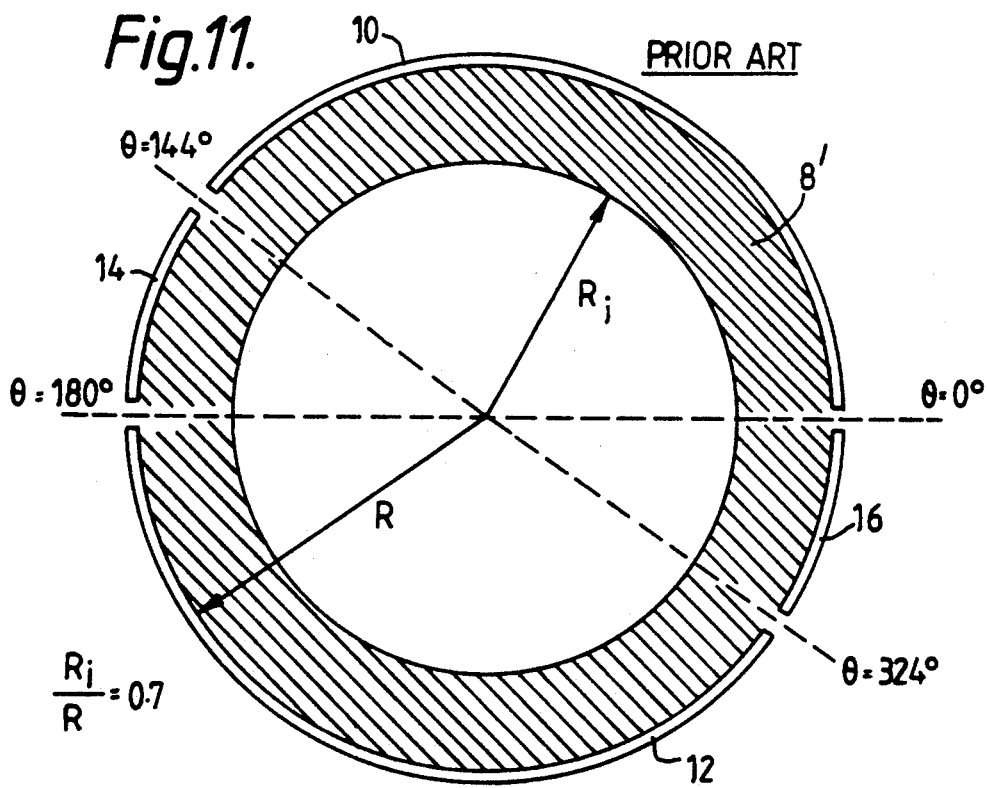
FIG. 11 shows the prior art construction.

FIG. 11 shows the prior art device described in EP 0,308,004 in which the pipe 8 is replaced with a PTFE cylinder 8' which reduces the flowing radius of the pipe Ri to 70% of the radius of the electrodes R without interfering substantially with the measurement. In this case, the sensitivity shown in FIG. 3 is the worst situation for such a device.

Figure 12:
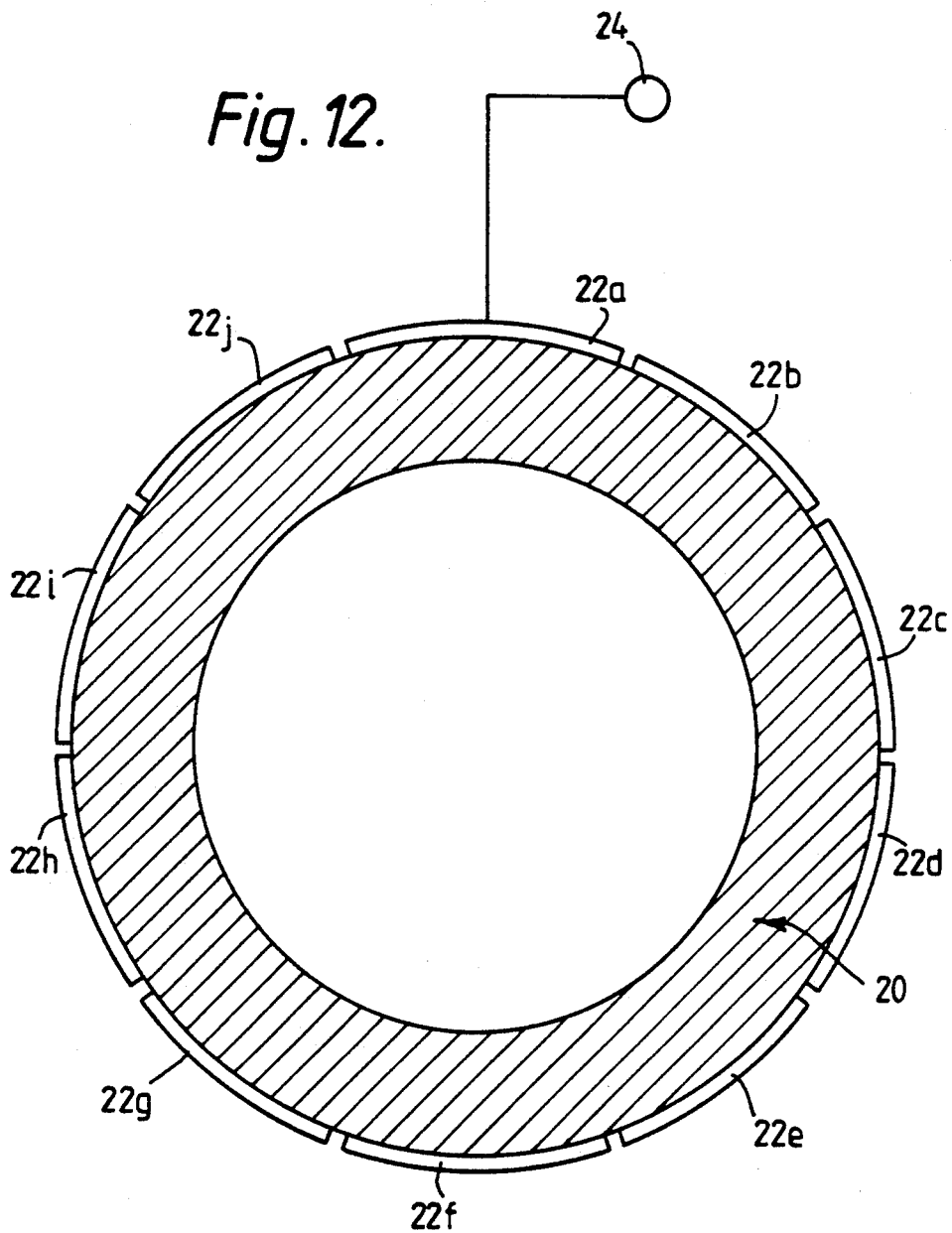
FIG. 12 shows a construction according to one aspect of the present invention.
Figure 13:
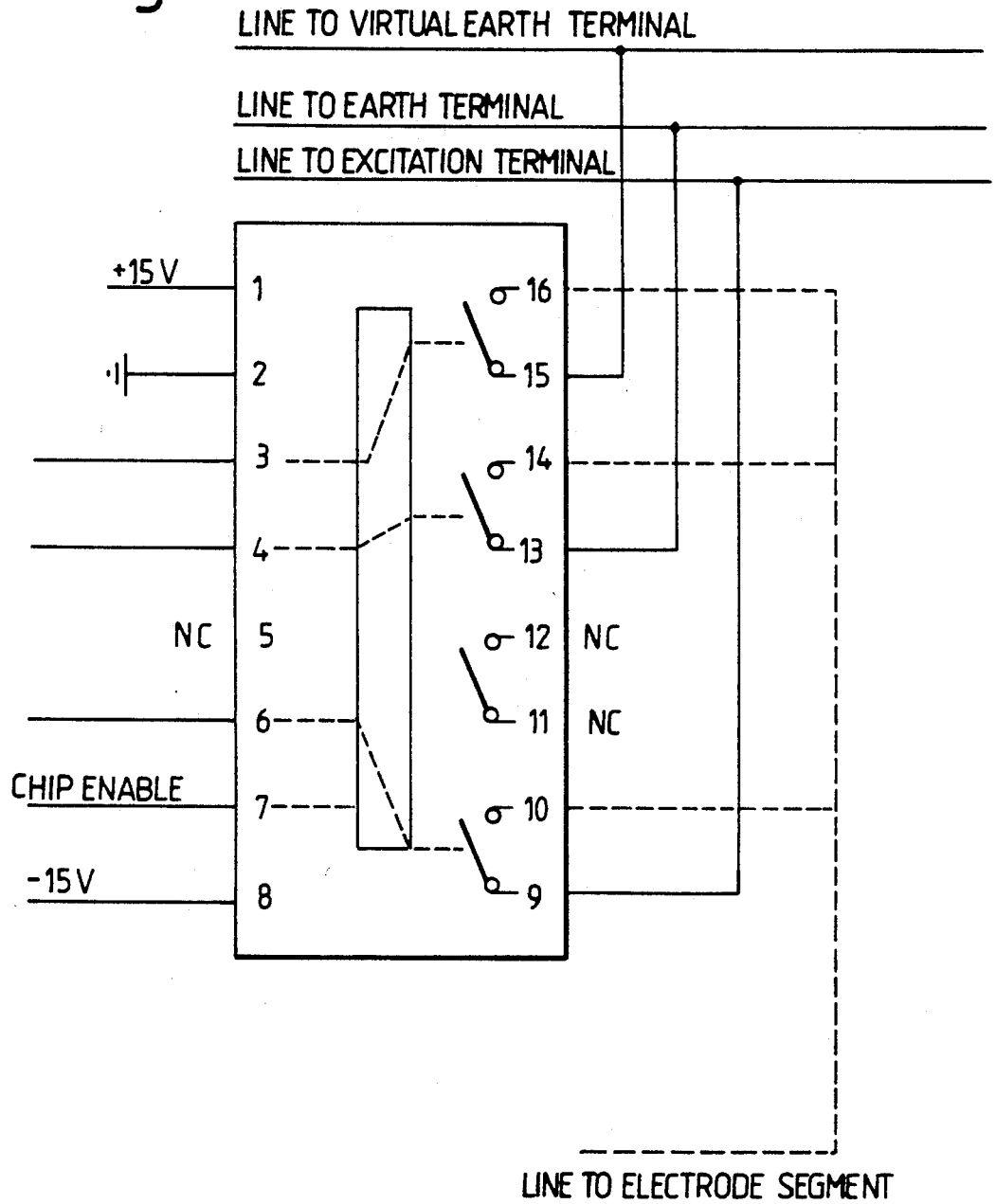
FIG. 13 shows one embodiment of a suitable switching arrangement to be used in the present invention.
Figure 15:
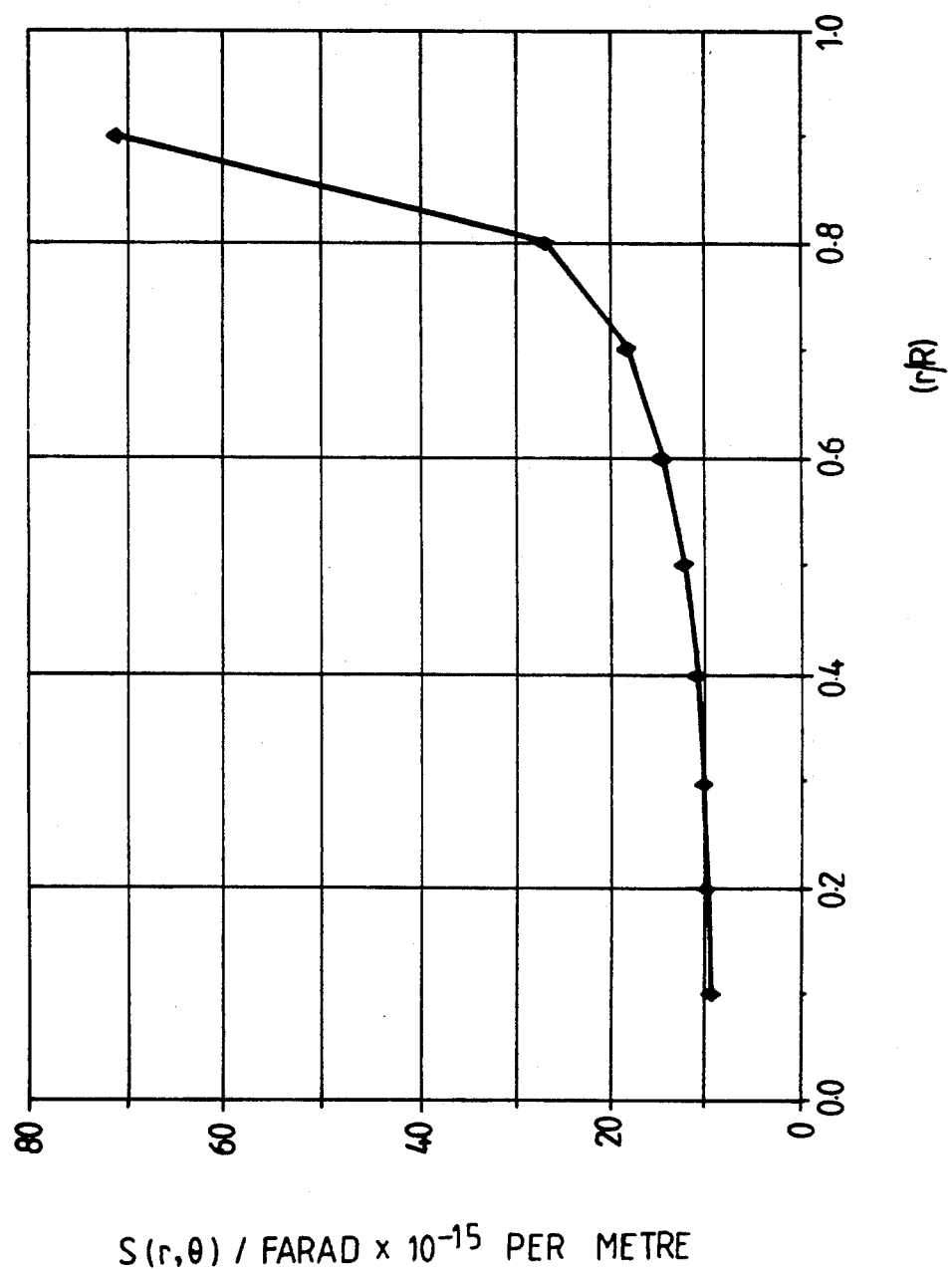
FIG. 15 shows the variation of mean field sensitivity with radial position for an embodiment of the present invention.
Figure 16:
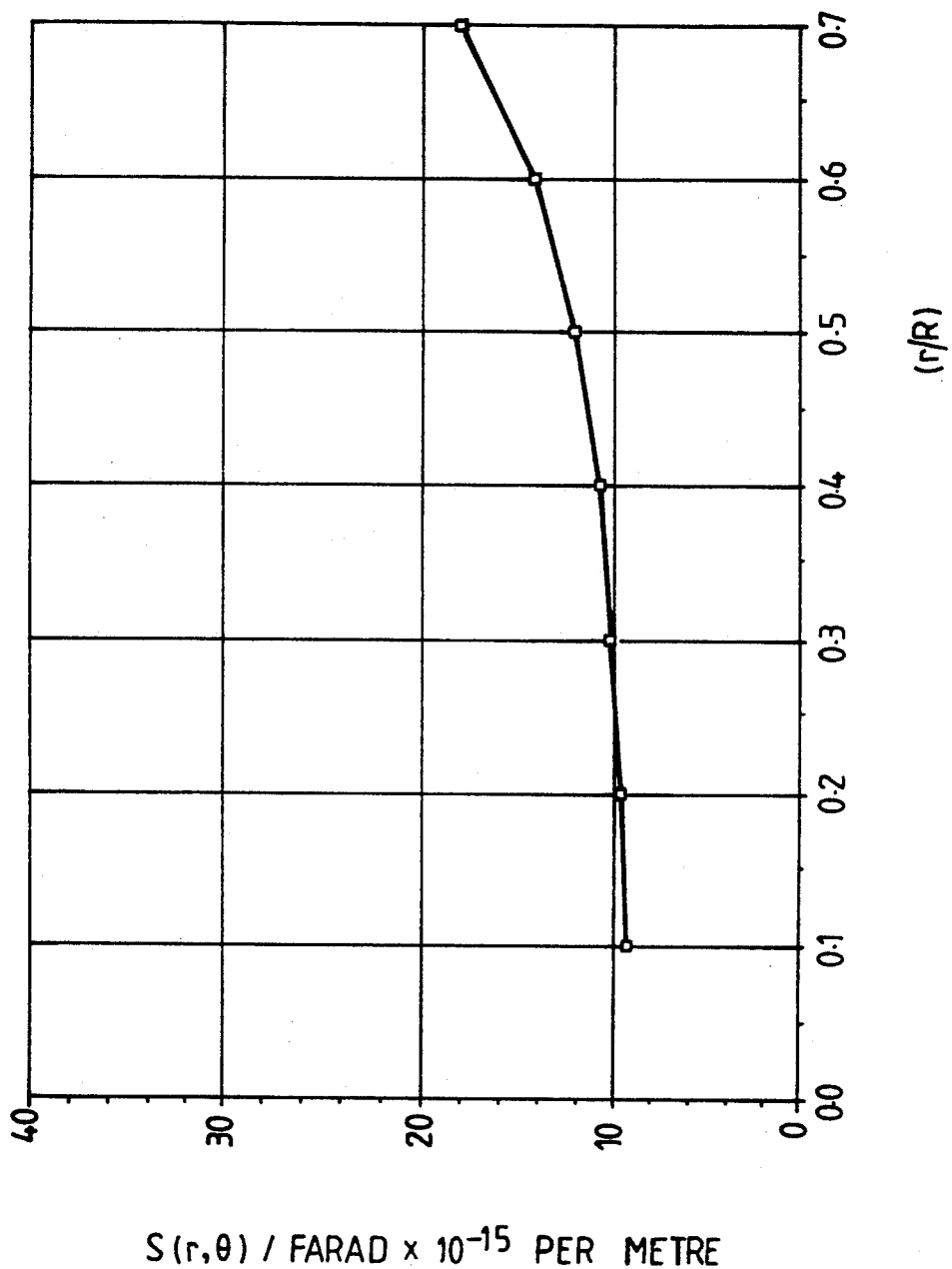
FIG. 16 shows the corresponding plot to FIG. 15 when a dielectric liner is used.

Referring now to FIG. 12, the embodiment of the invention shown therein comprises a capacitance void fraction measuring device comprising a Teflon cylinder 20, an internal radius of 40 mm being 70% of the external radius. The improvement in performance of this device can be seen by comparing FIGS. 15 and 16. FIG. 15 shows the radial variation in sensitivity for a device as shown in FIG. 10 while FIG. 16 shows the corresponding plot for the device of FIG. 12. As can be seen, the variation in sensitivity is much less in the latter case. Ten 36° electrodes 22a-j are mounted on the outer of the cylinder 20. Each electrode 22a-j is connected to an associated AD7590 analogue switch 24 (only 1 shown) controlled from the digital I/O port of a DELL 286 microcomputer. The switches 24 allow the electrodes to be connected, either individually or in groups, to the excitation, virtual earth or earth terminals of capacitance measurement circuitry. The connections for each AD7590 chip are shown in FIG. 13, each chip being identical. A schematic diagram of the capacitance measurement circuitry is shown in FIG. 14.

Figure 14:
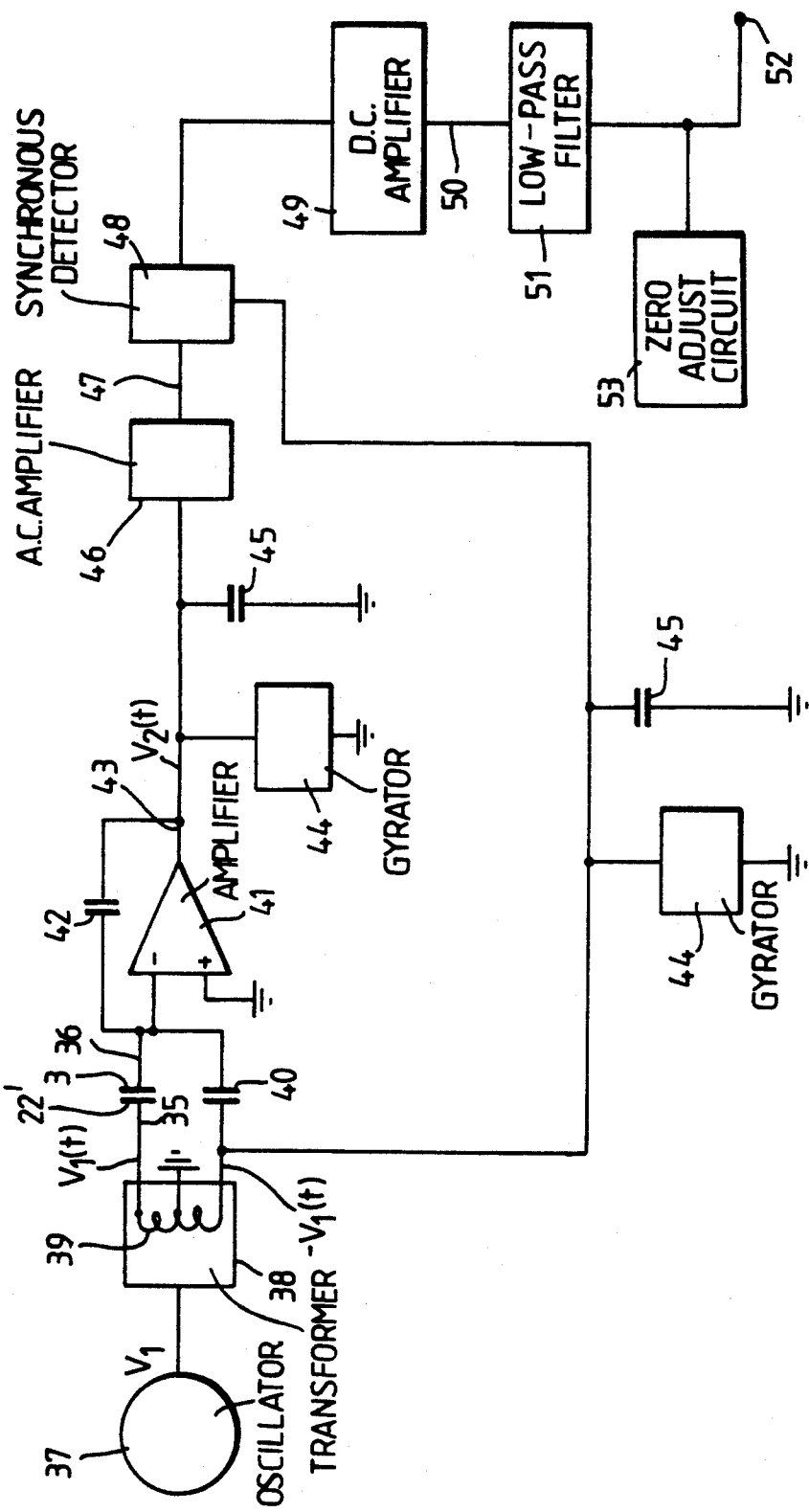
FIG. 14 shows one embodiment of capacitance measurement circuitry for use in the present invention.

Referring now to FIG. 14, a circuit to which the device of FIG. 12 is connected is illustrated. A 10 kHz oscillator 37 applies an excitation signal $V_1$ to a transformer 38 which has a secondary winding 39 producing outputs which are 180° out of phase with each other. One of these outputs 35 is applied to the excitation electrodes 22' of the device of FIG. 12 and the other output is applied to a reference capacitor 40. The capacitance of the reference capacitor 40 is substantially the same as the capacitance of the device illustrated in FIG. 12. The capacitor 40 and the virtual earth electrodes are connected via lead 36 to an amplifier 41. A capacitor 42 provides a feedback circuit for the amplifier 41 such that the signal $V_2(t)$ appearing at the output 43 of the amplifier is as follows:

$$V_2(t) = V_1(t)(C_x - C_{ref})/C_{fb}$$

where $V_1(t)$ if the signal applied at 35
$C_x$ is the capacitance of the sensor
$C_{ref}$ is the capacitance of the capacitor 40
$C_{fb}$ is the capacitance of the capacitor 42.

The signal on output 43 is passed via a bandpass filter, comprising an inductor or a gyrator 44 in parallel with a capacitor 45, to an AC amplifier 46. The gyrator 44 acts as a passive inductance and may be of conventional form comprising for example a type 353 operational amplifier, four resistors and a capacitor. The AC amplifier 46 provides a modulation input 47 to a synchronous detector 48. The synchronous detector also receives the signal applied to the capacitor 40 via a further bandpass filter comprising gyrator 44 and capacitor 45 which are identical to the like-numbered components connected to output 43. The two bandpass filters are tuned to the supply frequency 10 kHz. The synchronous detector 48 extracts the DC component of the output of the amplifier 46 and this is applied to a DC amplifier 49.

The output 50 of the amplifier 49 is passed through a low pass filter 51 to remove any residual 10 kHz signal. The resultant DC signal is applied to output terminal 52, a zero adjust circuit 53 being provided to calibrate the output 52. For example the circuit 53 can be used to adjust the output to zero when it is known that there are no bubbles between the electrodes device shown in FIG. 12.

In the procedures described below, at any given rotational position of the electrostatic field, four adjacent electrodes are connected to the excitation terminal of the capacitance measurement circuitry, four adjacent electrodes are connected to the virtual earth terminal and the remaining two are connected to the earth terminal to give rise to the optimised boundary electrode configuration described in connection with FIG. 10. Under the control the DELL microcomputer, the potentials applied to each of the electrodes are switched in such a way as to rotate the electrostatic sensing field, clockwise, in steps of 36°.

The terminal to which each electrode is connected for five consecutive rotation steps is shown in the table below. The pattern of changes is repeated up to the 10th position which completes the rotation of the field.

| electrode | position 1 | position 2 | position 3 | position 4 | position 5 | → | position 10 |
|---|---|---|---|---|---|---|---|
| 22 a | excitation | guard | virtual earth | virtual earth | virtual earth | → | excitation |
| 22 b | excitation | excitation | guard | virtual earth | virtual earth | → | excitation |
| 22 c | excitation | excitation | excitation | guard | virtual earth | → | excitation |
| 22 d | excitation | excitation | excitation | excitation | guard | → | guard |
| 22 e | guard | excitation | excitation | excitation | excitation | → | virtual |

-continued

| electrode | position 1 | position 2 | position 3 | position 4 | position 5 | → | position 10 |
|---|---|---|---|---|---|---|---|
| 22 f | virtual earth | guard | excitation | excitation | excitation | → | earth virtual earth |
| 22 g | virtual earth | virtual earth | guard | excitation | excitation | → | virtual earth |
| 22 h | virtual earth | virtual earth | virtual earth | guard | excitation | → | virtual earth |
| 22 i | virtual earth | virtual earth | virtual earth | virtual earth | guard | → | guard |
| 22 j | guard | virtual earth | virtual earth | virtual earth | virtual earth | → | excitation |

The procedure adopted to test the rotating field volume fraction device is described below. Firstly, the device is mounted in a three inch, inclinable flow loop. After appropriate flow conditions have been established, the electrostatic field is rotated in steps of 36° (as described above) and at each step, the system capacitance $C_{in}$ was measured using the ratio arm bridge circuitry, shown in FIG. 14, the result being stored in the memory of the DELL computer. For the ten angular positions of the electrostatic field, the suffix i above refers to the i'th such angular position. Furthermore, under a given set of flow conditions, the electrostatic field undergoes N complete revolutions in order to obtain a satisfactorily averaged result. The suffix n refers to the n'th of the revolutions. (For the experiments described herein, N was set equal to 10.) After N revolutions of the electrostatic field had been completed, an effective measured system measured system capacitance $C_{ef}$ was computed from:

$$C_{ef} = \sum_{i=1}^{10} \sum_{n=1}^{N} \frac{C_{in}}{10N}$$

The value of $C_{ef}$ was then stored on the hard disk of the DELL microcomputer along with details of the associated flow conditions.

Also, for each set of conditions, an average value of $C_{iav}$ of the measured capacitance for each of the 10 angular positions of the electrostatic field was computed from $$C_{iav} = \sum_{n=1}^{N} \frac{C_{in}}{N}$$

and the results were stored on the hard disk of the DELL microcomputer. The values of $C_{iav}$ under a given set of flow conditions can be used to investigate the response of a 'non-rotating field' device orientated at different angular positions with respect to the flow. Under a given set of flow conditions, changes in the response of a volume fraction device with its angular orientation give a good indication of the severity of spatial variations in the sensitivity of the electrostatic sensing field.

The device and procedures described above were used to investigate air/oil flows, where oil always formed the continuous component. Tests were performed at oil superficial velocities $U_{os}$ in the range $0.1 ms^{-1}$ to $0.2 ms^{-1}$, in flows deviated at 0°, 15° and 30° from the vertical, and at gas void fractions in the range 0 to 0.3. At each set of flow conditions, and at a gas void fraction $\alpha$, the parameter $C_{ef}(\alpha)$ was computed according to equation given above.

Figure 17:
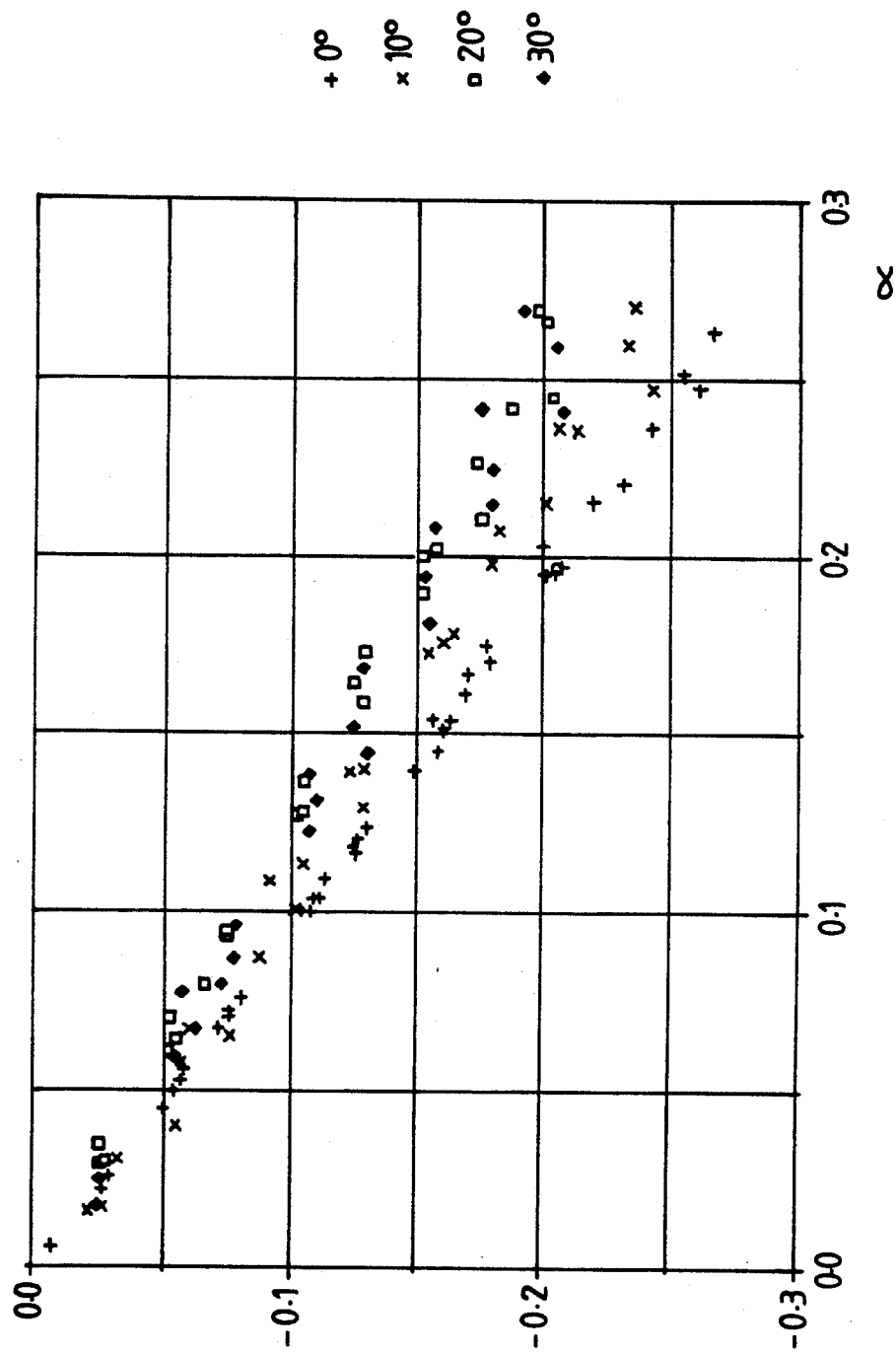
FIG. 17 shows the capacitance change versus air void fraction for a prior art device measuring flows in a deviated pipe at 0°, 10°, 20° and 30° from vertical.
Figure 18:
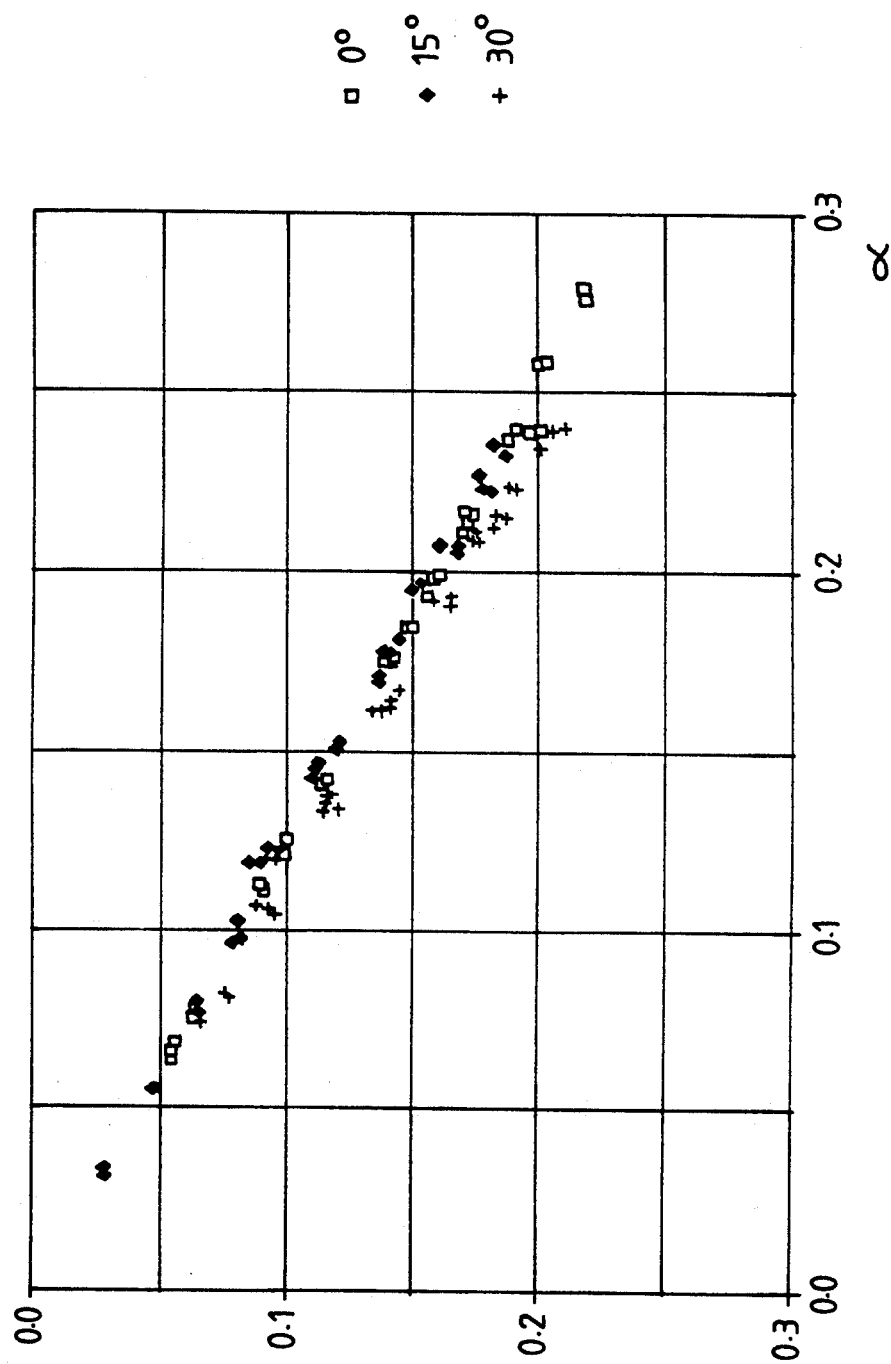
FIG. 18 shows the corresponding plot to FIG. 17 when an embodiment of the present invention is used at 0°, 15° and 30° from vertical.

FIG. 18 shows the quantity $C_{ef}(\alpha) - C_{ef}(0)$ plotted against void fraction $\alpha$ for all of the flow conditions that were investigated ($C_{ef}(0)$ represents the measured value of $C_{ef}$ when $\alpha$ is zero, i.e. when the flow loop working section is full of oil only). It is readily apparent from FIG. 18 that the deviation angle, and hence the phase distribution, has only a minimal effect on the response of the rotating field volume fraction device of the present invention. This result is significant when the gross differences in the local gas void fraction distribution which exist between vertical and deviated air/oil flows are considered. In vertical air/oil flows the local void fraction distribution is axisymmetric, with a peak value at the centre of the pipe, whereas in deviated flows the majority of the gas accumulates close to the upper side of the pipe. The results obtained from the rotating field device are compared with data obtained under similar conditions using more conventional capacitive volume fraction devices. Accordingly, FIG. 17 presents data which was obtained from a capacitive volume fraction device which incorporated a dielectric sleeve but which did not utilise the rotating field principle. This data was obtained at flow conditions similar to those used for the rotating field device and at deviation angles of 0°, 10°, 20° and 30° from the vertical. It is readily apparent from FIG. 17 that the flow deviation angle, and hence the local volume fraction distribution, has a significant effect on the response of this non-rotating field impedance volume fraction device.

Comparison of FIGS. 17 and 18 gives an excellent indication of the benefits to be obtained, in terms of reduced sensitivity to the phase distribution, from using e present invention.

We claim:

1. A multi-electrode capacitive apparatus for measuring multi-phase flows comprising:
   a) a pipe through which a flow is directed having electrodes disposed around a wall thereof,
   b) a switching arrangement,
   c) sensing means for connection to each electrode by means of said switching arrangement, said switching arrangement operating to vary the connection of the electrodes to the sensing means such that an electric field experienced by the flow within said pipe rotates, wherein said electrodes are connected so as to form an excitation group of adjacent electrodes and a detection group of adjacent electrodes, the excitation group and the detection group being of approximately the same size, and
   d) averaging means for determining an average capacitance measured over an integer number of rotations independently of phase distribution in the pipe.

2. An apparatus as claimed in claim 1, wherein the electrodes are connected in groups to the sensing means, a first group comprising the excitation group being connected to an excitation terminal of the sensing means, second and third groups being disposed on either side of the first group and connected to earth so as to act as guard electrodes and a fourth group comprising the detection group being connected to a virtual earth terminal of the sensing means.

3. An apparatus as claimed in claim 2, wherein the first group subtends an angle of substantially 144°, the second and third groups subtend angles of substantially 36° and the fourth group subtends an angle of substantially 144°.

4. An apparatus as claimed in claim 2, wherein ten electrodes are provided.

5. An apparatus as claimed in claim 4, wherein four adjacent electrodes are connected to an excitation terminal of the generation and sensing means, four adjacent electrodes are connected to a virtual earth terminal of said means and two electrodes are connected to an earth terminal of said means.

6. An apparatus as claimed in claim 1, wherein the electrodes are equally spaced around the pipe.

7. An apparatus as claimed in claim 1, wherein in order to rotate the electric field, the switching arrangement transfers the setting of each electrode to an adjacent electrode in the direction of rotation and a new flow measurement taken, this procedure being repeated until the original positional settings are resumed.

8. An apparatus as claimed in claim 1, wherein the pipe comprises a material of substantially the same dielectric constant as the multi-phase flow and the electrodes are separated from the flow by a thickness of material such that the sensitivity of the device due to the electric field experienced by the flow within the pipe is substantially uniform.

9. An apparatus as claimed in claim 8, wherein the ratio of the flowing radius of the pipe to the radius of the electrode arrangement is about 0.7.

* * * * *